United States Patent
Liu et al.

(10) Patent No.: US 10,870,823 B2
(45) Date of Patent: Dec. 22, 2020

(54) BIOMIMETIC DEVICE

(71) Applicant: Lehigh University, Bethlehem, PA (US)

(72) Inventors: Yaling Liu, Ambler, PA (US); Antony Thomas, Bethlehem, PA (US)

(73) Assignee: LEHIGH UNIVERSITY, Bethlehem, PA (US)

( * ) Notice: Subject to any disclaimer, the term of this patent is extended or adjusted under 35 U.S.C. 154(b) by 156 days.

(21) Appl. No.: 14/737,809

(22) Filed: Jun. 12, 2015

(65) Prior Publication Data

US 2015/0361386 A1 Dec. 17, 2015

Related U.S. Application Data

(60) Provisional application No. 62/078,471, filed on Nov. 12, 2014, provisional application No. 62/011,205, filed on Jun. 12, 2014.

(51) Int. Cl.
| | |
|---|---|
| C12M 3/06 | (2006.01) |
| C12M 1/12 | (2006.01) |
| C12M 1/00 | (2006.01) |

(52) U.S. Cl.
CPC ............ *C12M 23/16* (2013.01); *C12M 23/20* (2013.01); *C12M 25/02* (2013.01)

(58) Field of Classification Search
CPC ...... C12M 23/16; C12M 23/20; C12M 25/02; C12M 35/02; C12M 35/08; G01N 33/4836
See application file for complete search history.

(56) References Cited

U.S. PATENT DOCUMENTS

| | | | | |
|---|---|---|---|---|
| 2004/0245102 | A1* | 12/2004 | Gilbert ................. | B01D 63/087 204/451 |
| 2010/0240086 | A1* | 9/2010 | Kashanin .......... | B01L 3/502753 435/29 |
| 2012/0211373 | A1* | 8/2012 | El-Sayed ............... | C12M 23/16 205/778 |

* cited by examiner

*Primary Examiner* — William H. Beisner
*Assistant Examiner* — Danielle B Henkel
(74) *Attorney, Agent, or Firm* — The Belles Group, P.C.

(57) ABSTRACT

Described herein are apparatus comprising: a first layer comprising a first microfluidic channel; a second layer comprising a second microfluidic channel; and a membrane for culturing cells; along with methods of making and using same.

19 Claims, 3 Drawing Sheets

BIOMIMETIC DEVICE

CROSS-REFERENCE TO RELATED PATENT APPLICATIONS

This application claims the benefit of U.S. Provisional Application Ser. No. 62/078,471, filed Nov. 12, 2014, entitled "Biomimetic Channel for In Vitro Blood Vessel Modeling and Evaluation of Targeted Nanoparticle Delivery"; and U.S. Provisional Application Ser. No. 62/011,205, filed Jun. 12, 2014, entitled "A Microfluidic Device", the contents of which are hereby incorporated herein in their entirety.

This invention was made with government support under R15 EB015105 awarded by the National Institutes of Health. The government has certain rights in the invention.

BACKGROUND

Endothelial cells (ECs) form the inner lining of blood vessels and are exposed to dynamically varying factors like hemodynamic conditions (shear stress, laminar, turbulent flow), biochemical signals (cytokines) and interaction with other cell types (smooth muscle cells, monocytes, platelets, etc.). Blood vessel functions are regulated by an interaction between these factors. The occurrence of a pathological condition can lead to localized upregulation of cell adhesion molecules on the EC lining of the blood vessels. This process is promoted by circulating cytokines such as tumor necrosis factor-alpha (TNF-α), which leads to expression of, inter alia, intercellular adhesion molecule-1 (ICAM-1) on the EC surface. ICAM-1 molecules are critical in regulating EC layer dynamic integrity and cytoskeletal remodeling, and they also mediate cell-cell interactions as part of inflammatory responses and wound healing. ICAM-1 molecules on the EC layer surface are therefore a potential target for therapeutic agents for various pathological conditions.

Targeted drug delivery systems hold promise for innovative medical treatment for various pathological conditions. Conventional animal models raise ethical concerns and the correlation between animal and human models is often unpredictable. In vivo studies are also constrained by their limited control over heterogeneous physical, chemical, and biological parameters influencing the blood vessel, as well as challenges with imaging. Conventional in vitro platforms lack the functionality, security and pace demanded by today's pharmaceutical research.

Thus, there remains a need for practical, human-centered and biomimetic devices that are inexpensive to manufacture and easy to integrate with state-of-the-art analysis platforms. By coupling potential EC surface markers with carefully engineered drug carriers, effective and active vascular drug delivery systems can be achieved. The devices should also be capable of operating with minimal sample volumes and delivering better signal to noise ratios than animal models. Embodiments of the present invention are directed to meeting these needs.

SUMMARY

In some embodiments, the present invention provides an apparatus comprising: a first layer comprising a first microfluidic channel; a second layer comprising a second microfluidic channel; and a membrane for culturing cells.

In other embodiments, the present invention provides for the use of an apparatus as described herein for quantifying vascular permeability. Still further embodiments provide for the use of an apparatus as described herein for evaluating drug particle delivery and uptake.

Yet other embodiments provide systems for evaluation drug particle binding.

DETAILED DESCRIPTION

As used herein, the term "superior" in the context of the first layer and second layer, refers to the first layer being positioned on top of the second layer.

As used herein, the terms "upper layer", "upper channel", "first layer", "first channel", and "apical layer" are used interchangeably.

As used herein, the terms "bottom layer", "bottom channel", "second layer", "second channel", and "basal layer" are used interchangeably.

As used herein, the terms "device" and "apparatus" may be used interchangeably.

In some embodiments, ECs are grown on a porous semi-permeable membrane to form an EC layer. In some embodiments, the porous semi-permeable membrane separates an upper channel (e.g. first layer) from a lower channel (e.g. second layer). In some embodiments, the upper and lower channels are made of polydimethylsiloxane (PDMS). In some embodiments, the EC layer is treated with an amount of TNF-α effective to result in expression of ICAM-1 on the EC layer surface.

In some embodiments, anti-ICAM-1 coated particles of different antibody coating densities are used to evaluate the binding affinity of anti-ICAM-1 coated particles for the ICAM-1 expressed on the EC layer surface. In some embodiments, this binding affinity is evaluated under physiologically relevant fluid shear stress (e.g. from about 6 dyne/cm$^2$ to about 18 dyne/cm$^2$).

Figure 1:
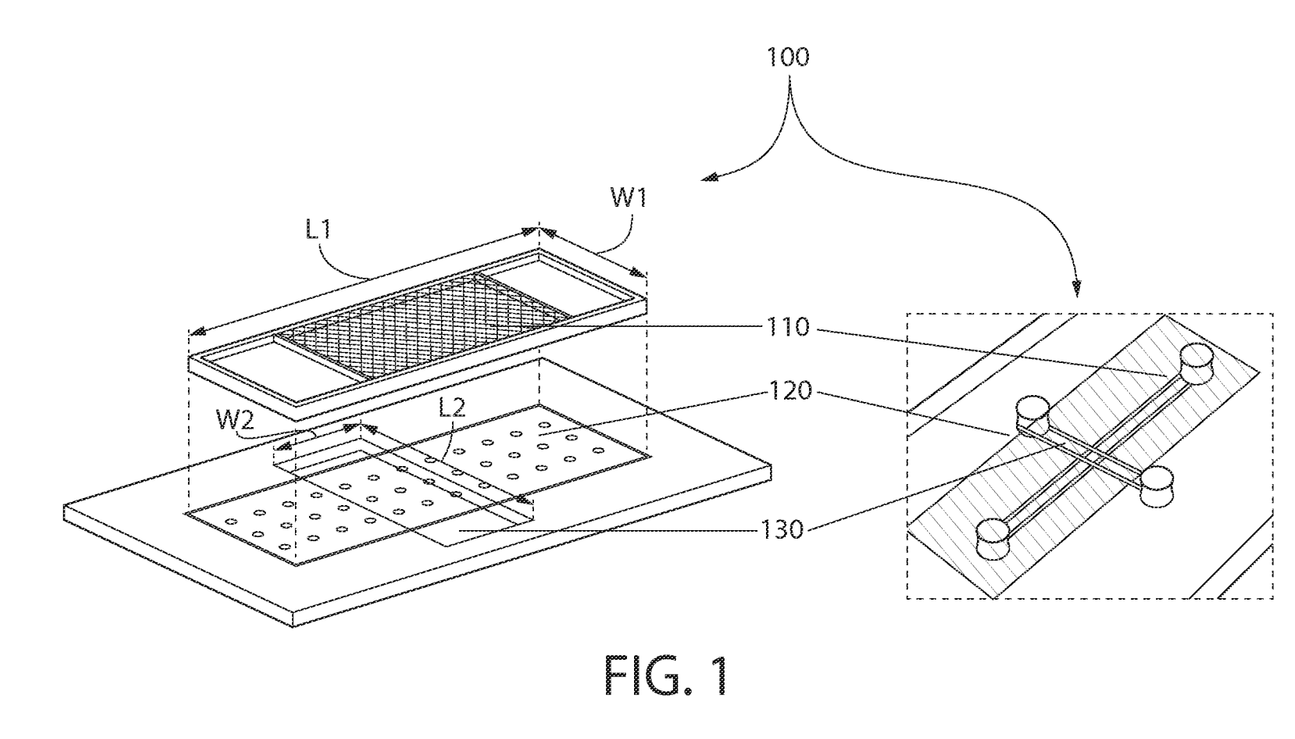
FIG. 1 depicts two perspectives of an exemplary apparatus of the present invention

In some embodiments, the present invention provides an apparatus (or device) 100 comprising: a first layer comprising a first microfluidic channel 110; a second layer comprising a second microfluidic channel 130; and a membrane for culturing cells 120. In some embodiments, the apparatus or devices of the present invention may also be referred to as a "chip" or "micro-chip".

In some embodiments, a portion of the membrane for culturing cells is semi-permeable. In some embodiments the membrane for culturing cells comprises pores. In some embodiments, the membrane for culturing cells is positioned between the first layer and the second layer.

In other embodiments, the first layer and second layer comprise an elastomeric material. In further embodiments, the elastomeric material is selected from an organosilicon, silicon, glass, polystyrene, polyvinyl chloride, polymethyl methacrylate, cyclic olefin copolymer, polycarbonate and a combination of two or more thereof. Still further embodiments provide an apparatus wherein the elastomeric material is an organosilicon. In some embodiments, the organosilicon is PDMS. In some embodiments, the first layer and second layer comprise the same material. In some embodiments, the first layer and second layer comprise different materials.

In some embodiments, the membrane for culturing cells comprises a material selected from a polycarbonate, a polyester, polyethylene terephthalate, a mixed cellulose ester, PDMS and a combination of two or more thereof. In other embodiments, the membrane for culturing cells comprises a polycarbonate.

In some embodiments, the first layer is positioned superior to the second layer. In some embodiments, the membrane for culturing cells is coupled to the first layer.

In some embodiments, the membrane for culturing cells is in fluid communication with the first layer. In other embodiments, the membrane for culturing cells is in fluid communication with the second layer.

In some embodiments, the first layer and the second layer are in an offset arrangement. In some embodiments, the offset arrangement creates a plurality of sections. In other embodiments, the first layer and second layer are arranged perpendicular to each other. In still further embodiments, the first layer and the second layer are in a parallel arrangement.

In some embodiments, the membrane for culturing cells is adapted to culture a plurality of cell lines. In other embodiments, the membrane for culturing cells comprises a first major surface and a second major surface. In some embodiments, the first major surface of the membrane for culturing cells is adapted to culture a first cell line and the second major surface is adapted to culture a second cell line. In some embodiments, the first cell line comprises ECs. Yet further embodiments provide an apparatus wherein the second cell line comprises smooth muscle cells, tumor cells, stem cells, alveolar cells, epithelial cells, nerve cells, hepatic cells or a combination thereof.

In some embodiments, the first microfluidic channel and the second microfluidic channel comprise an inlet and an outlet.

In some embodiments, for example as shown in FIG. 1, the first layer 110 has a length L1 and a width W1; and the second layer 130 has a length L2 and a width W2.

Further embodiments provide an apparatus wherein the first layer has a length of from about 1 mm to about 10 cm. In some embodiments, the first layer has a length of from about 10 mm to about 5 cm. In some embodiments, the first layer has a length of from about 50 mm to about 4 cm. In some embodiments, the first layer has a length of from about 100 mm to about 3 cm. In some embodiments, the first layer has a length of from about 500 mm to about 2.5 cm. In other embodiments, the first layer has a length of about 2 cm.

In some embodiments, the first layer has a width of from about 20 microns to about 10 cm. In some embodiments, the first layer has a width of from about 50 microns to about 1 cm. In some embodiments, the first layer has a width of from about 100 microns to about 500 mm. In some embodiments, the first layer has a width of from about 200 microns to about 250 mm. In some embodiments, the first layer has a width of from about 250 microns to about 1 mm. In some embodiments, the first layer has a width of from about 300 microns to about 500 microns. In further embodiments, the first layer has a width of about 350 microns.

Other embodiments provide an apparatus wherein the second layer has a length of from about 1 mm to about 10 cm. In some embodiments, the second layer has a length of from about 10 mm to about 5 cm. In some embodiments, the second layer has a length of from about 50 mm to about 4 cm. In some embodiments, the second layer has a length of from about 100 mm to about 3 cm. In some embodiments, the second layer has a length of from about 500 mm to about 2.5 cm. In other embodiments, the second layer has a length of about 2 cm.

In some embodiments, the second layer has a width of from about 20 microns to about 10 cm. In some embodiments, the second layer has a width of from about 50 microns to about 1 cm. In some embodiments, the second layer has a width of from about 100 microns to about 500 mm. In some embodiments, the second layer has a width of from about 200 microns to about 250 mm. In some embodiments, the second layer has a width of from about 250 microns to about 1 mm. In some embodiments, the second layer has a width of from about 300 microns to about 500 microns. In further embodiments, the second layer has a width of about 350 microns.

In some embodiments, the membrane for culturing cells is substantially similar in dimension to the first layer.

Still further embodiments provide for the use of an apparatus as described herein for quantifying vascular permeability. Some embodiments of the present invention provide methods for quantifying vascular permeability comprising provide a device as described herein, wherein the device comprises a membrane for culturing cells, and said membrane comprises at least one cell culture; providing a compound known to enhance vascular permeability and tagging it with a tracer molecule; contacting said cell culture, through said upper channel, with said compound known to enhance vascular permeability and said tracer molecule; recovering the quantity of tracer molecule recovered in the lower channel; and calculating the vascular permeability by comparing the quantity of tracer molecule recovered in the lower channel versus the amount of tracer molecule introduced through the upper channel.

Figure 2:
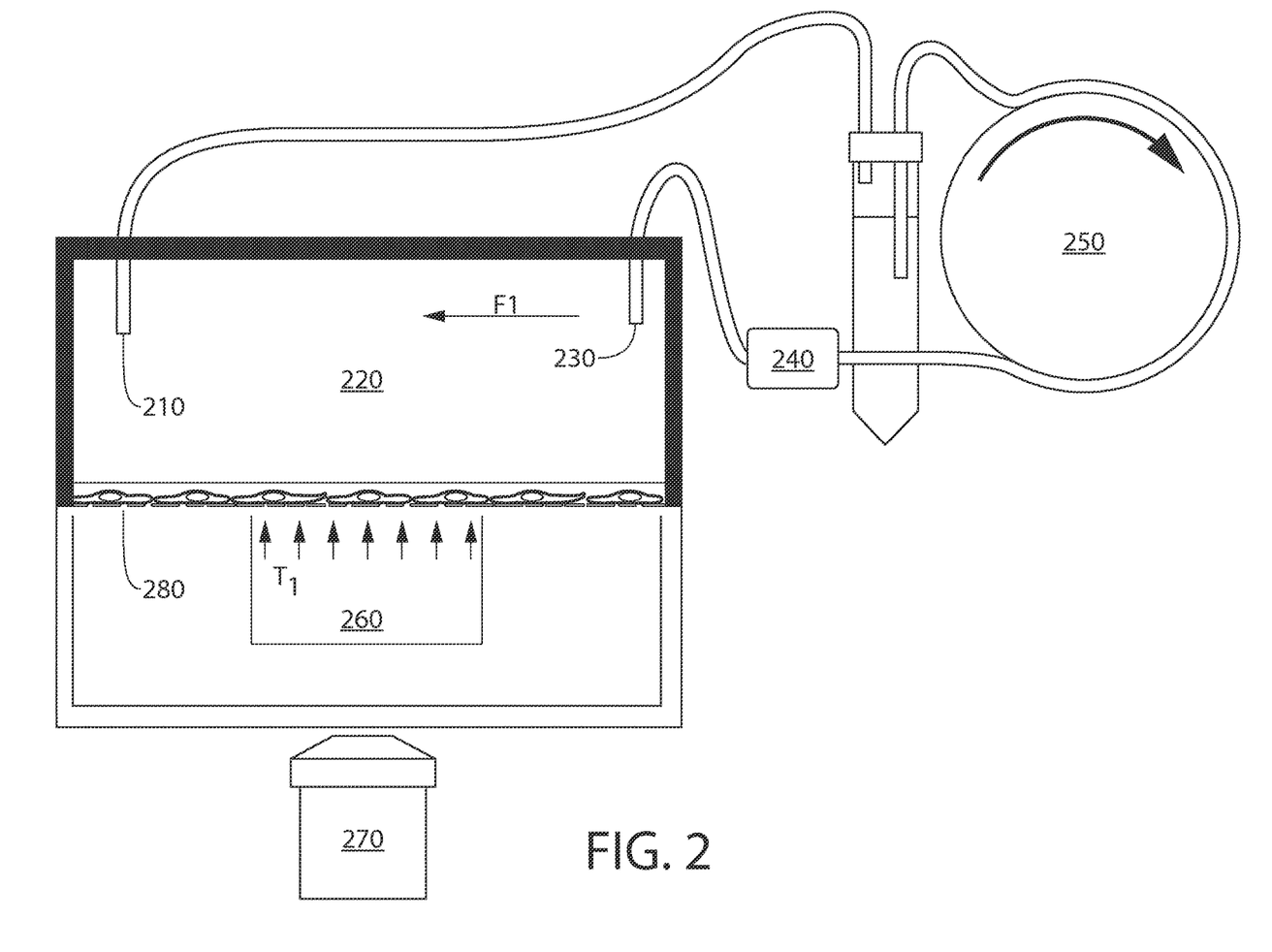
FIG. 2 depicts an exemplary system for evaluating particle binding using an exemplary apparatus of the present invention.

While other embodiments provide for the use of an apparatus as described herein for evaluating drug particle delivery and uptake. Some embodiments provide a system for evaluating particle binding 200, comprising a syringe pump 250, a heater 240, a device according to the present invention comprising an upper channel 220 and a lower channel 260, wherein the device further comprises an inlet 230 and outlet 210; and wherein the syringe pump controls the flow F1 across the semi-permeable porous membrane comprising a cell culture 280; and wherein the system is adapted to permit the cell culture to be treated T1 with an agent (e.g. TNF-α) known to induce expression of an inflammatory marker (e.g. ICAM-1) through the lower channel 260.

Figure 4:
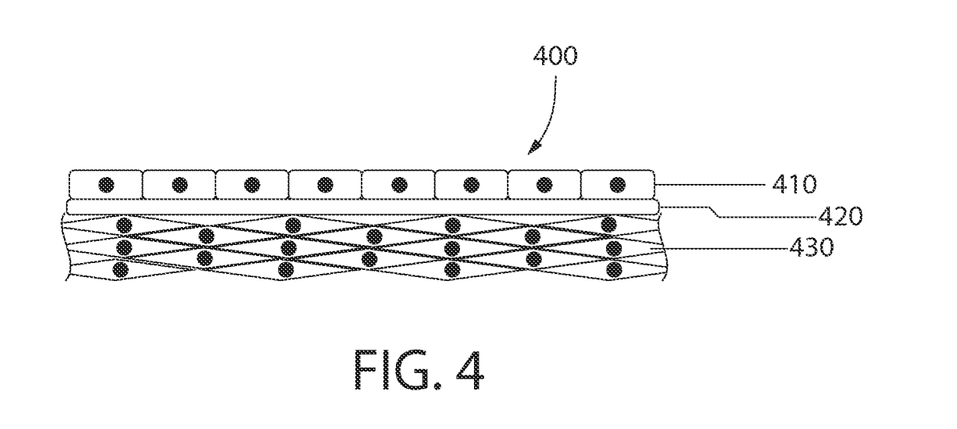
FIG. 4 depicts an assembly having a co-culture of a plurality of cell lines in accordance with certain embodiments of the present invention.

The interaction between EC and smooth muscle cell (SMC) plays an important role in EC permeability dynamics. As such, the ability of the devices of the present invention to co-culture a plurality of cell lines (e.g. ECs and SMCs) is an important attribute. In fact, in some embodiments, the dimensions and shape of the devices of the present invention can be tuned to fit the co-culture of SMCs along with ECs. In some embodiments, the lower channel is widened to increase the co-culture area. In some embodiments, both channels have the ability to be accessed separately. In other embodiments, the upper and lower channels along with the membrane are coated with 50 µg/ml fibronectin solution overnight at 37° C. In some embodiments, the devices of the present invention comprise an assembly 400 comprising a membrane for culturing a plurality of cell lines. In such embodiments, bovine aortic endothelial cells (BAOECs) 410 may be seeded onto the semi-permeable membrane 420 in the upper channel followed by bovine aortic smooth muscle cells (BAOSMCs) 430 seeding onto the semi-permeable membrane 420 in the lower channel. In some embodiments, the device is placed in an incubator under standard culture conditions (37° C. and 5% $CO_2$) for 4 hrs after both cases of cell seeding to allow cell attachment and spreading on the membrane. In some embodiments, media is frequently changed in both the channels. In some embodiments, confluent layers of BAOECs and BAOSMCs are grown in the upper and lower channels of an apparatus as described herein. In some embodiments, the ECs form a confluent monolayer while SMCs stack into multiple layers.

Signaling between ECs and SMCs is essential for maintaining tone in mature vessels, and their communication is critical during development, and for repair and remodeling associated with blood vessel growth. Therefore, some embodiments of the present invention are designed to facilitate the signaling between ECs and SMCs.

In tumor and other inflammatory tissues, interstitial fluid pressure (IFP) cannot be easily controlled. Also, tumor vessels show high permeability to fluid and macromolecules as a result of incomplete endothelial lining, discontinuous or absent basement membranes, and lack of pericyte coverage. In addition, transporting nanoparticles into solid tumors can be a challenge because of high fluid pressure. While the IFP in normal tissues is actively controlled and remains close to atmospheric levels, IFP in most human tumors is abnormally elevated.

In some embodiments, ECs are cultured under physiological levels of flow in the upper channel. Some embodiments mimic an IFP by introducing a pressure gauge into the flow injection system, with the outlet excluded. In some embodiments, for example as shown in FIG. 2, a syringe pump 250 (Harvard Apparatus) and a pressure sensor (Apollo Electronics Co Ltd.) are used to develop and gauge the pressure respectively. In some embodiments, the syringe pump 250 is initially set at a high flow rate F1 (at approximately 30-50 µl/min) to let the pressure in the lower channel reach the desired level and then the flow rate F1 is adjusted to stabilize the pressure. In some embodiments, the effect of high IFP in the lower channel 260 on the EC layer will be characterized, with a focus on cytoskeletal remodeling and cell-cell binding integrity. In other embodiments, the extent of trans-endothelial transport of tracer molecules/model drug carriers through the EC layer will be evaluated under similar conditions. In some embodiments, the present invention provides methods wherein the EC layer in the upper channel is exposed to inflammatory agents and the higher IFP is maintained in the lower channel to understand the right antibody agents that can facilitate the highest binding and trans-endothelial delivery.

As discussed, tumor associated blood vessels have high permeability leading to elevated interstitial fluid pressure and altered flow patterns within the tumor microenvironment. These aberrant hydrodynamic stresses and other tumor-EC interactions are critical in enhancing tumor development by stimulating the angiogenic activity of ECs lining the tumor vasculature. Currently it is not known to what extent these factors affect endothelial organization. Reproducing a tumor microenvironment consisting of blood vessels and tumor cells in vitro is particularly challenging. However, some embodiments of the present invention can be used to evaluate 3D tumor-endothelium interactions.

In some embodiments, 3D tumor models are grown in the lower channel. In some embodiments, a cancer cell line (e.g. PC3, MCF 7, or HCT116) is mixed with hydrogel (Collagen I or IV, matrigel) and infused into the lower channel of the blood vessel model using a syringe tubing setup. In some embodiments, the cancer cells form a 3D tumor model in an incubator under cell culture friendly conditions. In other embodiments, ECs are seeded in the upper channel and grown under flow. In further embodiments, constant perfusion of media in the upper channel provides both the EC layer and tumor model with growth media. In some embodiments, devices of the present invention are able to characterize EC-tumor model crosstalk through an evaluation of specific EC receptor expression and cytoskeletal remodeling. In some embodiments, the devices of the present invention can be used to study tumor metastasis and extravasations and endothelial angiogenesis.

Embodiments of the present invention can also be used to evaluate the stem cells, which is critical for the development of new therapeutics. To more closely mimic the in vivo microenvironment and for better understanding of its complexity, and the factors that regulate the mesenchymal stem cell (MSC) activity, embodiments of the present invention can characterize the co-culture of MSCs with ECs.

Embodiments of the present invention provide several key features not offered by existing technologies. For example, embodiments of the present invention are able to: 1) closely mimic in vivo healthy and diseased blood vessel conditions in the same channel; 2) grow multiple cell lines; and 3) provide customizable channels.

The bi-layer assemblies of the present invention also allow for locally triggered receptor expression on cells that mimic vascular disease. In some embodiments, the devices of the present invention allows control and target cells to be grown on the same device, integrated in situ imaging and testing, patient specific vascular geometry and flow condition, and fast parametric evaluation with minimal sample volume. The introduction of this bi-layer semi-permeable membrane provides the devices of the present invention the advantage of a more realistic model of the boundary regions in the body where two types of tissue interact. The ability to more closely mimic conditions found in vivo, allows for studies where exchange occurs within the human body. Phenomena such as nutrient exchange from digestive to circulatory tracts and gaseous exchange in the respiratory tract to tissues can also be studied.

Introduction of this key semi-permeable membrane allows for an advantage in studies related to exchange, uptake and delivery, above and beyond what existing technologies offer.

In some embodiments, the present invention comprises a semi-permeable membrane with hundreds of nanometers to a few micron pores. In some embodiments, devices of the present invention permit a section of the upper channel to be accessed independently, which facilitates spatially controlled and localized cytokine activation of ECs. Having both direct cytokine activated and non-activated ECs in the same channel allows investigating the transition in surface receptor expression in the EC microenvironment and the role of flow in it.

The devices of the present invention have an unprecedented ability to investigate the microenvironment of ECs, and acquire real-time data. In some embodiments, the devices mimic the native environment for ECs by facilitating in vivo levels of flow and biomolecule supply, along with an opening for localized access. The ability to characterize particle binding per cell for a FSS range of 6-18 $dyne/cm^2$ using 210 nm particles, enables the device to evaluate the suitability and efficacy of candidates for drug delivery.

In some embodiments, the microfluidic channels comprise complex channel geometries such as a bifurcation geometry, vascular-network like hierarchically branching geometry, or channel geometry reconstructed from MRI/CT scanned vascular images.

EXAMPLES

Example 1

Blood vessel mimicking channels are fabricated on a silicon wafer and casted out of PDMS. The master for fabricating the channels is patterned on a silicon wafer using SU-8 2050 photoresist (MicroChem Corp.). Sylgard 184 PDMS (Dow Corning Corp.) is prepared according to manufacturer's instruction and cast over the photoresist pattern. The upper channel is 350 microns wide and 100 microns tall, and the lower channel is 1000 microns wide and 100 microns tall. A polycarbonate (PC), track-etched thin clear membrane (Whatman, GE Healthcare) with 1 micron diameter pores and an average calculated pore density of $1.5*10^7$ pores/cm$^2$ is embedded between two PDMS channels. The PDMS slabs containing the top and bottom channels are carefully peeled off the master template. The PDMS undergoes extended baking (4 hours at 80° C.) to ensure complete cross-linking of monomers, and any remaining monomers are extracted by soaking ethanol overnight.

The bottom PDMS channel is kept thin to facilitate microscopy based imaging using higher magnification. The bottom PDMS channel is bonded to a thin glass slide. The top and bottom PDMS layers are bonded to the PC membrane using a PDMS mortar film, which is a mixture of PDMS pre-polymer (10:1 ratio of base and curing agent) with toluene in equal proportion and a thin layer (~2-3 microns) is obtained by spin-coating on a glass slide at 1500 rpm for sixty (60) seconds.

PDMS channel sides are stamped onto this thin film. The PC membrane is placed between the PDMS channels, and they are aligned. After they are aligned, the composite is placed in an oven at sixty degrees centigrade (60° C.) overnight for curing the PDMS mortar. Inlet and outlet ports are punched to provide access to the top and bottom channels.

Such bilayer PDMS channels separated by a semi-permeable membrane provide a platform to culture a cell layer and to flow/inject different liquids toward the cell layer.

Example 2

NeutrAvidin coated 210 nanometer and 1 micron fluorescent particles (Invitrogen Corp.) were diluted to $10^{10}$ and $10^9$ particles/mL respectively using BlockAid™ solution (Invitrogen Corp.) and sonicated. Biotinylated Protein G (29988, Thermo Scientific) diluted in 1% BSA solution is bound to the NeutrAvidin coating on the particles. ICAM-1/Control IgG (or both) antibody (NB500-318 Novus Biologicals) with specificity for bovine cells to the Protein G coated particles. The particles are incubated for 12 hours on a shaker at 4 C for both coating steps and the unbound protein G/antibody is removed by centrifugation. The particles are also washed in 1% BSA solution to remove any leftover unbound protein G/antibody, and the particles are diluted to their respective working concentrations (see Table 1 below).

TABLE 1

| Particle Size | Final Particle Concentration | Total Particle Volume (μm$^3$) |
|---|---|---|
| 210 nm | 4.77 * 10$^9$/mL | 2 × 10$^7$ |
| 1 micron | 3.85 * 10$^7$/mL | 2 × 10$^7$ |

The concentration of the particles available is analyzed on a microplate reader at 485 nanometers (nm) excitation/530 nm emission and compared to a calibration curve constructed from stock particle solution.

Anti-ICAM-1 coating density on the particle is determined using ELISA. 210 nm particles are conjugated with anti-ICAM-1 at 100% (maximum) and 50% of coating density, while the 1 micron particles are all coated with 100% of coating density. ELISA is performed using a HRP conjugated anti-mouse k-light chain specific monoclonal antibody to characterize the particle surface antibody density for both micro/nano particles. The specificity of the reagent to mouse antibody light chains provides a direct measurement of the anti-ICAM-1 binding sites available on the particle. Particles are incubated with 5% HRP conjugated anti-mouse k-light chain specific monoclonal antibody for 30 minutes, followed by washing with 1% BSA solution and clearing out of unbound antibody through centrifugation. 50 μl of the particle solution are loaded on a 96-well plate and the particle concentration is analyzed. Then 50 μl of Amplex Ultra Red reagent is added to each well and the reaction is allowed to proceed for 10 minutes at room temperature. The fluorescence intensity of the particle sample with Aplex Ultra Red reagent is observed on a microplate reader at 544 nm excitation/590 nm emission. The fluorescence intensities are converted to the number of HRP molecules using the calibration curves prepared using biotinylated-HRP conjugation.

Assuming a 1:1 binding ratio between anti-ICAM-1 and secondary antibody, the anti-ICAM-1 density on the particles are determined. 210 nm and 1 μm particle antibody coating density based on fluorescence intensity is compared to estimate the relative accuracy of the technique.

Complete saturation of anti-ICAM-1 coating on 210 nm particles produced 232.5±25 anti-ICAM-1/particle and this is brought down to 112.9±19 anti-ICAM-1/particle as well using control IgG antibody. These correspond to 1851.2±199/μm$^2$ for the maximum antibody density case and 898.9±151 anti-ICAM-1/μm$^2$ respectively. 1 μm particles have an antibody density of 2367.8±264 anti-ICAM-1/particle which corresponds to 232.9±25 anti-ICAM-1/μm$^2$.

This example demonstrates an inventive method through which the devices of the present invention can be used to characterize the binding dynamics of nanoparticles and microparticles.

Example 3

Primary bovine aortic endothelial cells (BAOECs) are cultured in hepes buffered DMEM supplemented with 10% heat activated fetal bovine serum (Atlanta Biologicals, Inc.) and 1% penicillin-streptomycin (Sigma-Aldrich). A device, such as one prepared according to the method described in Example 1, is sterilized under UV light overnight. Prior to cell seeding, the upper channel and membrane of the device are coated with 50 μg/ml fibronectin solution (Sigma-Aldrich) and incubated overnight at 37° C. The channels are rinsed with media to remove any excess, unattached fibronectin. BAOECs are seeded onto the porous semi-permeable membrane at a density of $2*10^7$ cell/ml. The seeded device is placed in an incubator under standard culture conditions (37° C. and 5% $CO_2$) overnight to allow cell attachment and spreading on the membrane. The upper channel is then subjected to flow based media change at low FSS (0.01 dyne/cm2) to provide a constant supply of fresh media to the BAOECs without being subjected to FSS effects.

Example 4

BAOECs are subjected to a FSS of 12 dyne/cm². This physiologically relevant FSS was calculated using the following equation:

$$\tau_{cell}=6\mu Q/wh^2$$

The flow is brought about using a high precision and extremely low pulsation peristaltic pump (ISMATEC, IPC-N series), which allows multiplex access to the flow channel, providing the flexibility of introducing new entities (e.g. particles or specific biomolecules) without disturbing the laminar FSS to which the BAOECs are exposed.

The process described herein illustrates how the devices and systems of the present invention can be used to study the effects of a heterogeneous environment on the ECs, with precise control over the time of treatment for each factors.

Example 5

BAOECs are subjected to at least 24 hours of flow at 12 dyne/cm² and then treated with TNF-α to activate ICAM-1 expression on the EC layer. Treatment is performed on an 80-90% confluent cell layer. BAOECs are locally activated by introducing DMEM media containing 10 Units (U)/ml of TNF-α for 2 hours in the lower channel of the device. TNF-α diffuses through the porous semi-permeable membrane separating the upper and lower channels and spatially controls the direct activation of BAOECs only present above the lower channel. BAOECs on the the upstream or downstream sections of the upper channel do not come in direct contact with the inflammatory cytokine. The BAOECs are cytokine treated from the basal (lower) side of the cell layer.

The process described herein mimics the triggering of ECs from the tissue side, which is akin to what happens in human physiology. It demonstrates that embodiments of the present invention can be used to evaluate the triggering of ECs from the tissue side as well as the blood vessel lumen side (e.g. as described below in Example 6).

Example 6

To understand the effect of basal versus apical cell side TNF-α treatment on surface ICAM-1 expression, a particle binding study is performed on cells cytokine treated from both basal and apical sides. TNF-α is added to media and flowed in the upper channel to perform the apical side EC treatment study.

For example, as shown in FIG. 2, particles are introduced at their respective concentrations for designated flow times, flow time being controlled by the syringe pump 250, without stopping the flow and while TNF-α activation T1 of ECs is still conducted from the lower channel 260. This permits the study to most closely mimic the native environment. The particle working concentrations are chosen such that the total volume of particles remains constant. In order to ensure the total number of particles/flow case remains constant for all particle binding FSS cases, flow time is decreased with increases in FSS.

Particles are infused into the upper channel 220; and after their designated flow time unbound particles are removed by flushing with buffer solution containing a plasma membrane stain (CellMask™, Life Technologies) to fluorescence tag the BAOECs. Particle bound BAOECs are then fixed in paraformaldehyde (3.7%). The extent of particle binding is analyzed by phase contrast and fluorescence microscopy (FV1000-IX81, Olympus) and image analysis is performed using ImageJ software.

Example 7

To further examine the state of BAOECs under flow in an exemplary device of the present invention, actin assembly characteristics are studied. ECs exposed to FSS undergo a change in cell shape and their microfilament network remodels and align to the direction of flow. We examined this by staining F-actin stress fibers of BAOECs growing in the upper channel. The exposure of cells to flow at 12 dynes/cm² results in alteration of cell shape from the typical cobblestone pattern to fusiform as observed in ECs in vivo. The cells and their actin stress fibers uniformly align in the direction of flow. The control (no flow) has the F-actin fibers arranged in a radial pattern or emerging from the edges, a mechanism to maintain the cell well-spread. To assess the relationship between cell orientation and flow direction, the angle (α) between the orientation of stress fibers and the width (short-axis) of the microchannel is plotted. It is observed that for the control, the stress fibers align at an average angle of 51.4°, while the cells exposed to flow show an average angle of 90.1°.

The thickness of the cortical actin and width of stress fibers are calculated from the fluorescence labeled actin cytoskeleton images. In BAOECs subjected to 12 dyne/cm² of FSS for 4 hrs, the thick cortical actin is found to reorganize into actin stress fibers along the direction of flow. About 2 fold decrease in thickness of cortical actin is observed. The width of stress fibers increases around 2 fold as well for BAOECs subjected to FSS.

Since the actual aggregate of stress fibers cannot be understood from analyzing the width of the stress fibers alone (thickness of stress fibers in the z direction not considered), their fluorescence intensity is quantified in grayscale value. Multiple but less intense stress fiber distribution is observed across the cytoplasm of BAOECs for the no flow case based on fluorescence intensity. BAOECs subjected to flow have fewer but more profound and sharp stress fiber distribution. Stress fiber density in the cells is quantified through a line profile across the cytoplasm of BAOECs and using ImageJ software to calculate fluorescence intensity. The software identifies stress fibers by their increased fluorescence relative to areas devoid of stress fibers. Sharp, distinct peaks represent individual stress fibers, while the width and fluorescence intensity of the peak indicate the thickness of a stress fiber. Thin and thick actin stress fibers are quantified for both control and FSS samples by classifying stress fibers based on fluorescence intensity (grayscale value). For statistical purposes, stress fibers with fluorescence intensity ≤50 grayscale value are arbitrarily marked as thin and >50 as thick. The no flow sample has almost an equal distribution of thin and thick stress fibers, while the BAOECs subjected to FSS have a significant distribution of thick stress fibers in its cytoplasm. Laminar and sustained FSS induces thicker stress fiber organization of ECs along with the direction of flow along with maintaining elongated cell morphology.

Cell cytoskeletal arrangement patterns are an important indicator of its state and response to external stimuli. The characteristics of F-actin stress fiber rearrangement of ECs on exposure to flow in embodiments of the present invention is close to that observed in vivo and displays the biomimetic nature thereof.

Example 8

The role of flow on particle binding is studied. Specifically, surface ICAM-1 expression on BAOECs in upstream, TNF-α activated and downstream in a particle binding study is evaluated. 210 nm particles with coating densities of 232.5±25 and 112.9±19 anti-ICAM-1/particle are flowed at 6, 12 and 18 dyne/cm$^2$ after the BAOECs are treated with TNF-α for 2 hrs under a steady and sustained FSS of 12 dyne/cm$^2$.

BAOECs in the TNF-α activated section have around 4-5 times higher particle binding density compared to the upstream section for the different FSS for 210 nm particle with a coating density of 232.5±25 anti-ICAM-1/particle. This clearly shows significant increase in surface ICAM-1 expression in BAOECs at the TNF-α activated section. The downstream section of the channel also shows significantly higher (around 2 times) particle binding density compared to the upstream section. Thus the BAOECs in the downstream section have elevated surface ICAM-1 expression versus upstream. Particle binding per cell for 210 nm particles with an anti-ICAM-1 coating density of 112.9±19/particle showed a similar trend. The results of these experiments demonstrate that there is significantly higher particle binding density for the TNF-α activated and downstream sections compared to the upstream section of the channel.

When compared to the 232.5±25 anti-ICAM-1/particle case, the particle binding density is around half for the 112.9±19/anti-ICAM-1 particle case. For both anti-ICAM-1 coating density cases the particle binding density decreases when the FSS increases from 6 to 12 dyne/cm$^2$. However, particle binding density doesn't show much influence to FSS as it increases beyond 12 dyne/cm$^2$.

Example 9

In order to study the transition in ICAM-1 expression in the different sections (upstream, TNF-α treated and downstream) of the channel, these sections are divided into further segments and evaluated along the length of the channel. The increase in particle binding as a result of ICAM-1 expression by BAOECs begins in the upstream section of the channel very close to the TNF-α treated section. Particle binding characteristics remain comparable across the TNF-α treated section and are sustained in the nearby downstream regions. Particle binding in the downstream section is significantly higher than that of the upstream section, both not being TNF-α treated directly. There is a smooth decrease in particle binding along the channel length in the downstream section. After a channel length of about 3 mm, the particle binding density becomes comparable to that of upstream region. The increase in particle binding in the upstream section close to the TNF-α treated section and along the length of the downstream section may be due to a synergistic influence of flow and TNF-α effusion to the upper channel through the BAOEC layer which has increased permeability in the TNF-α treated region. Flow directed from the TNF-α activated to the downstream section carries a majority of the diffused TNF-α molecules towards the downstream section. The exposure to TNF-α leads to upregulation of ICAM-1 expression on BAOECs here, which decays along the channel length possibly due to the dilution of TNF-α to a negligible concentration.

Example 10

F-actin stress fiber arrangement after TNF-α treatment along the channel length is evaluated to further understand the EC microenvironment. A BAOEC layer was exposed to 4 hrs of FSS at 12 dyne/cm$^2$; followed by 2 hrs of localized TNF-α treatment (10 U/ml) from the lower channel. The cells are stained for F-actin stress fibers and their arrangement is studied in the upstream, TNF-α treated and downstream sections. BAOECs exposed to FSS in the upstream section have stress fibers aligned to flow direction as observed earlier. After 2 hr exposure to TNF-α, there is a thinning of stress fiber filaments in the central area of the cell cytoplasm. This thinning starts around the border of upstream and TNF-α treated sections. It is consistently observed throughout the TNF-α treated section and continues towards the downstream section. The F-actin stress fiber thickness in the cell center increases smoothly to levels comparable to the upstream section after about 1 mm length in the downstream section. Rearrangement in F-actin stress fibers is also observed in BAOECs after TNF-α treatment. These isolated disruptions of F-actin lattice are sparsely observed in the upstream regions close to TNF-α treated section, while it is more common in the TNF-α treated section. This is observed in the downstream section as well but the frequency of occurrence reduces along the channel length.

This demonstrates that embodiments of the present invention allow for the study of the micro-environmental dynamics of ECs when triggered locally. Specifically, Examples 8, 9 and 10 demonstrate the dynamics of surface-ICAM-1 expression and F-actin arrangement in different sections of the channel after localized TNF-α treatment.

Example 11

To demonstrate the applicability of our platform towards real time in situ studies we characterized dynamic binding of anti-ICAM-1 coated nanoparticles (NPs) to BAOECs being subjected to TNF-α treatment. The enclosed nature of exemplary devices of the present invention allows maintenance of sterile conditions.

Figure 3:
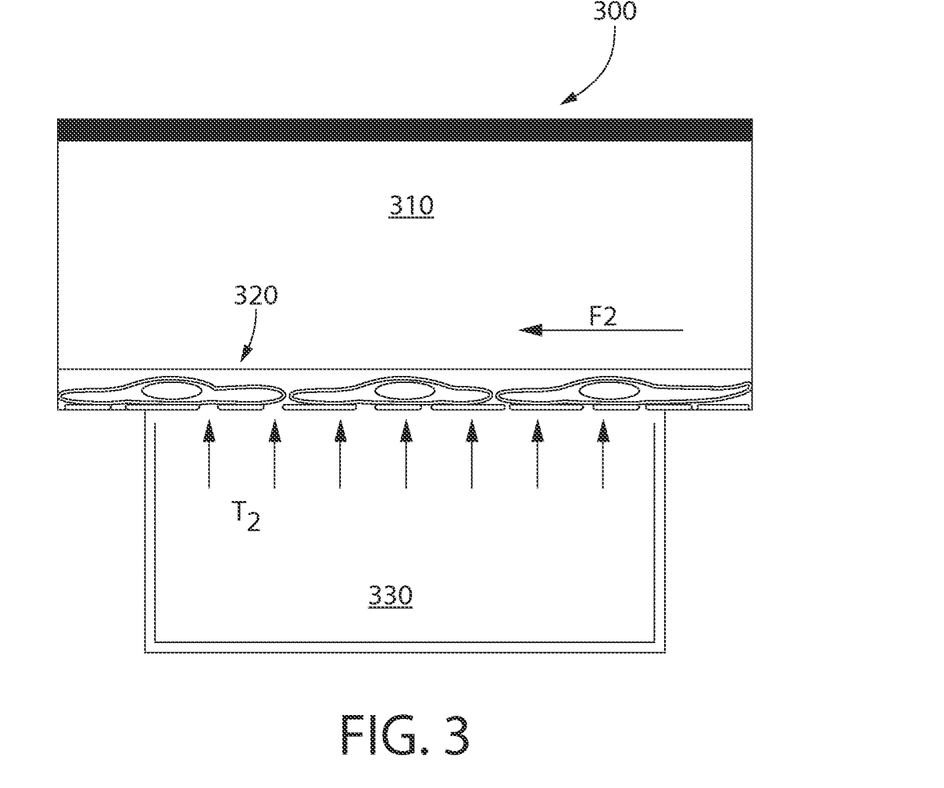
FIG. 3 depicts an experimental set-up for evaluating vascular permeability using an exemplary apparatus of the present invention.

As shown in FIG. 3, BAOECs 320 are subjected to 12 dyne/cm$^2$ of FSS for 6 hrs before localized TNF-α treatment T2 from the lower channel 330 while a steady flow F2 is continued in the upper channel 310. Real time binding of anti-ICAM-1 coated 210 nm particles (232.5±25 anti-ICAM-1/particle) is analyzed to characterize the dynamic nature of ICAM-1 expression by BAOECs. The cells are cultured in HEPES buffered media. A syringe pump, not shown but similar to that depicted in FIG. 2, controls the flow rate of the media and an in-line solution heater, also not shown but similar to that depicted as 240 in FIG. 2 (Warner Instruments, SH-27B), maintained the media temperature at 37° C. In some embodiments, such as the one shown in FIG. 2, the objective of the microscope is covered with a thin-film heating band 270 (Bioptech, 150819) to facilitate live cell imaging as optical coupling medium (oil) can act as a thermal coupling medium and draw heat away from the device.

The real time in situ particle binding study on live cells gives a clear idea of the dynamics in ICAM-1 upregulation over time for BAOECs. A steady FSS of 12 dyne/cm$^2$ is maintained and anti-ICAM-1 coated 210 nm particles are flowed before and while TNF-α treatment was performed. The particle binding per cell gives a quantified account of the surface ICAM-1 expression by the BAOECs and the characterization over time gives details on the dynamics of ICAM-1 upregulation. The particle binding density is analyzed at the TNF-α treated section of the upper channel. It is observed that there is a linear increase in ICAM-1 upregulation over time which saturates after approximately 3 hours and 20 minutes of TNF-α activation. Prior studies have not been able to provide quantified real time data to investigate the dynamic nature of ICAM-1 expression by ECs in an in vivo like platform.

Example 12

As a proof-of-concept demonstration of using our biomimetic vessel platform to understand the increase in vessel permeability under physiological conditions, we quantified the dynamics and kinetics of cell permeability caused by thrombin on BAOECs using our biomimetic blood vessel model. Fluorescent FITC sodium salt and FITC-Dextran (Sigma) of 376 and 4000 Da molecular weight are used as tracer molecules at 0.625 and 5 mg/ml respectively. The desired tracer molecule is flowed along with thrombin in the luminal upper channel, and the extent of tracer molecule permeation to the abluminal lower channel is a direct indication of the level of vessel permeability. This is monitored in real time by withdrawing 6 μl samples from the outlet of the lower channel at 10 minute intervals. These samples are analyzed photometrically using Infinite 200 PRO NanoQuant microplate readers at 490 nm excitation and 521 nm emission. The volume of buffer solution in the lower channel is maintained a constant by adding 6 μl of PBS to the inlet before withdrawing the data sample.

The data sample is collected from the lower abluminal channel every 10 min. Tracer molecule concentration is quantified by comparing the fluorescent intensity of the collected data sample to a concentration calibration curve. It is observed that for both tracer molecules, the concentration in the lower channel starts to increase acutely within 10 min of thrombin treatment and reaches the max value (0.09 mg/ml for FITC sodium salt and 0.34 mg/ml for FITC-Dextran 4 kDa) within 20-30 minutes. This means the permeability or gap formation of the EC monolayer initializes rapidly under flow and reaches its maximum within 20-30 minutes. There is an increase of around 3.5 times in permeability for both tracer molecules by then, and this increase is a direct measure of the change in endothelial cell-cell gap formation. Then, a fall in abluminal concentration of tracer molecule is observed which plateaus to a minimum value at about 60-70 minutes. This drop signifies the decrease in EC permeability due to the reduction in intercellular gaps and increase in barrier integrity with thrombin treatment time. FITC sodium salt and FITC-dextran are flowed at different concentrations in the luminal channel for ease of photometrical detection and analysis.

The versatility of our device allows to study the effect of heterogeneous triggering using different inflammatory mediators form the basal and apical EC sides, while the cells are cultured under flow. Thus when compared to traditional in vitro cell culture systems our device can mimic conditions closer to the physiologically relevant ones.

It is intended that any patents, patent applications or printed publications, including books, mentioned in this patent document be hereby incorporated by reference in their entirety.

As those skilled in the art will appreciate, numerous changes and modifications may be made to the embodiments described herein, without departing from the spirit of the invention. It is intended that all such variations fall within the scope of the invention.

The invention claimed is:

1. An electrode-free apparatus comprising:
a first layer formed of polydimethylsiloxane, the first layer comprising a first microfluidic channel having a first length and a first width, the first width being uniform along the first length of the first microfluidic channel;
a second layer formed of polydimethylsiloxane, the second layer comprising a second microfluidic channel having a second length and a second width, the second width being uniform along the second length of the second microfluidic channel, the second width being at least twice as wide as the first width;
a membrane for culturing cells, the membrane having a length that is at least the same as either the first or second length and a width that is at least the same as either the first or second width, and the membrane having a first major surface and a second major surface; and
wherein the membrane is bonded to each of the first layer and the second layer by a polydimethylsiloxane mortar film having a thickness ranging from about 2 microns to about 3 microns, and wherein the membrane is configured to have a layer of first cells disposed on the first major surface of the membrane facing the first microfluidic channel or a layer of first cells disposed on the second major surface of the membrane facing the second microfluidic channel.

2. The apparatus according to claim 1, wherein a portion of the membrane for culturing cells is semi-permeable and is positioned between the first layer and the second layer.

3. The apparatus according to claim 1, wherein the first layer and second layer comprise the same material.

4. The apparatus according to claim 1, wherein the membrane for culturing cells comprises a material selected from a polycarbonate, a polyester, polyethylene terephthalate, a mixed cellulose ester, PDMS and a combination of two or more thereof.

5. The apparatus according to claim 1, wherein the membrane for culturing cells is in fluid communication with one or both of the first and second layers.

6. The apparatus according to claim 1, wherein the first layer and the second layer are in an offset arrangement and the offset arrangement creates a plurality of sections.

7. The apparatus according to claim 1, wherein the first layer and the second layer are in a parallel arrangement.

8. The apparatus according to claim 1, wherein the membrane for culturing cells is coupled to the first layer.

9. The apparatus according to claim 1, wherein the membrane for culturing cells is adapted to culture a plurality of cell lines.

10. The apparatus according to claim 1, wherein the first cells are endothelial cells or tumor cells.

11. The apparatus according to claim 1, further comprising a layer of second cells disposed on a surface of the membrane facing the second microfluidic channel.

12. The apparatus according to claim 11, wherein the first cells are endothelial cells and the second cells are smooth muscle cells or tumor cells.

13. The apparatus according to claim 1, wherein the first width is 350 microns and the second width is 1,000 microns.

14. The apparatus according to claim 1, further comprising a treatment agent provided in one of the first and second microfluidic channels.

15. The apparatus according to claim 14, wherein the treatment agent is tumor necrosis factor-alpha (TNT-a).

16. The apparatus according to claim 1, further comprising a tracer molecule provided in one of the first and second microfluidic channels.

17. The apparatus according to claim 16, wherein the tracer molecule is one or a combination of fluorescent FITC sodium salt and FITC-Dextran.

18. An electrode-free apparatus comprising:
- a first layer comprising a first microfluidic channel forming a first flow direction, the first microfluidic channel having a first height of about 100 microns a first width of about 350 microns as measured perpendicular to the first flow direction;
- a second layer comprising a second microfluidic channel forming a second flow direction, the second microfluidic channel having a second height of about 100 microns and a second width of about 1,000 microns as measured perpendicular to the second flow direction;
- a membrane for culturing cells, the membrane having a first major surface and a second major surface, the membrane comprising pores extending between the first and second major surfaces, whereby the membrane has an average pore density of about $1.5 \times 10^7$ pores/$cm^2$; and
- a layer of first cells disposed on the first major surface of the membrane facing the first microfluidic channel or a layer of first cells disposed on the second major surface of the membrane facing the second microfluidic channel;

wherein the first microfluidic channel overlaps the second microfluidic channel at an intersection point, and at the intersection point the first flow direction is perpendicular to the second flow direction.

19. An electrode-free apparatus comprising:
- a first layer formed of polydimethylsiloxane, the first layer comprising a first microfluidic channel having a first height of about 100 microns, a first length, and a first width of about 350 microns, the first width being uniform along the first length of the first microfluidic channel;
- a second layer formed of polydimethylsiloxane, the second layer comprising a second microfluidic channel having a second height of about 100 microns, a second length, and a second width of about 1,000 microns, the second width being uniform along the second length of the second microfluidic channel, the second width being wider than the first width;
- a membrane for culturing cells, the membrane having a length that is at least the same as either the first or second length and a width that is at least the same as either the first or second width, and the membrane having a first major surface and a second major surface, the membrane comprising pores extending between the first and second major surfaces, whereby the membrane has an average pore density of about $1.5 \times 10^7$ pores/$cm^2$; and wherein the membrane is bonded to each of the first layer and the second layer by a polydimethylsiloxane mortar film having a thickness ranging from about 2 microns to about 3 microns, and wherein the membrane is configured to have a layer of first cells disposed on the first major surface of the membrane facing the first microfluidic channel or a layer of first cells disposed on the second major surface of the membrane facing the second microfluidic channel.

* * * * *